(12) United States Patent
Albright (10) Patent No.: US 7,530,963 B2
(45) Date of Patent: May 12, 2009

(54) METHOD OF MAINTAINING PATENCY OF OPENING IN THIRD VENTRICLE FLOOR

(75) Inventor: A. Leland Albright, Pittsburgh, PA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 777 days.

(21) Appl. No.: 10/424,023

(22) Filed: Apr. 24, 2003

(65) Prior Publication Data

US 2004/0211433 A1 Oct. 28, 2004

(51) Int. Cl.
*A61M 5/00* (2006.01)
*A61F 2/04* (2006.01)

(52) U.S. Cl. .......................................... 604/8; 623/23.7
(58) Field of Classification Search ........................ None
See application file for complete search history.

(56) References Cited

U.S. PATENT DOCUMENTS

| | | | | |
|---|---|---|---|---|
| 3,894,541 A * | 7/1975 | El-Shafei | ..................... | 604/10 |
| 4,106,510 A * | 8/1978 | Hakim et al. | .................. | 604/9 |
| 4,377,169 A * | 3/1983 | Banks | ........................... | 604/8 |
| 5,000,731 A * | 3/1991 | Wong et al. | ..................... | 604/8 |
| 5,332,402 A | 7/1994 | Teitelbaum | ..................... | 623/2 |
| 5,405,316 A * | 4/1995 | Magram | .......................... | 604/8 |
| 5,632,762 A | 5/1997 | Myler | ......................... | 606/194 |
| 5,782,798 A * | 7/1998 | Rise | ............................. | 604/500 |
| 5,957,949 A | 9/1999 | Leonhardt et al. | ........... | 606/194 |
| 6,162,172 A | 12/2000 | Cosgrove et al. | | |
| 6,190,353 B1 * | 2/2001 | Makower et al. | ......... | 604/95.01 |
| 6,263,237 B1 * | 7/2001 | Rise | .............................. | 607/3 |
| 6,383,159 B1 * | 5/2002 | Saul et al. | ....................... | 604/9 |
| 6,575,928 B2 * | 6/2003 | Saul et al. | ....................... | 604/9 |
| 6,655,386 B1 * | 12/2003 | Makower et al. | ........... | 128/898 |
| 6,875,192 B1 * | 4/2005 | Saul et al. | ....................... | 604/9 |
| 7,025,739 B2 * | 4/2006 | Saul | ............................. | 604/9 |
| 7,059,330 B1 * | 6/2006 | Makower et al. | ........... | 128/898 |
| 7,150,737 B2 * | 12/2006 | Purdy et al. | ................. | 604/506 |
| 7,189,221 B2 * | 3/2007 | Silverberg et al. | ......... | 604/500 |
| 2002/0173742 A1 | 11/2002 | Keren et al. | | |
| 2004/0211433 A1 * | 10/2004 | Albright | .................... | 128/898 |
| 2004/0215323 A1 * | 10/2004 | Stiger | ........................ | 623/1.15 |
| 2007/0179426 A1 * | 8/2007 | Selden | .......................... | 604/8 |

FOREIGN PATENT DOCUMENTS

| | | |
|---|---|---|
| EP | 0 920 842 | 6/1999 |
| WO | WO 97/13471 | 4/1997 |
| WO | WO 00/69365 | 11/2000 |
| WO | WO 00/78222 | 12/2000 |

OTHER PUBLICATIONS

Stiger, U.S. Appl. No. 10/423,147, entitled "Membrane Eyelet", filed Apr. 24, 2003.
Stiger et al., U.S. Appl. No. 10/423,144, entitled "Flow Sensor Device for Endoscopic Third Ventriculostomy", filed Apr. 24, 2003.

* cited by examiner

*Primary Examiner*—Thomas J Sweet
(74) *Attorney, Agent, or Firm*—Michael Best & Friedrich LLP (57) ABSTRACT

A method of maintaining the patency of an opening in a floor of a third ventricle includes forming the opening is the floor of the third ventricle. A stent is inserted into the opening and the stent is deployed into the opening. The stent becomes engaged with the floor and prevents the opening from closing.

5 Claims, 8 Drawing Sheets

METHOD OF MAINTAINING PATENCY OF OPENING IN THIRD VENTRICLE FLOOR

BACKGROUND OF THE INVENTION

1. Field of the Invention

The present invention relates to a medical method. More particularly, the present invention relates to a method for maintaining an opening or orifice in a septum (or membrane).

2. Description of the Related Art

Noncommunicating hydrocephalus is a condition that results in the enlargement of the ventricles caused by abnormal accumulation of cerebrospinal fluid (CSF) within the cerebral ventricular system.

In noncommunicating hydrocephalus there is an obstruction at some point in the ventricular system. The cause of noncommunicating hydrocephalus usually is a congenital abnormality, such as stenosis of the aqueduct of Sylvius, congenital atresia of the foramina of the fourth ventricle, or spina bifida cystica. There are also acquired versions of hydrocephalus that are caused by a number of factors including subarachnoid or intraventricular hemorrhages, infections, inflammation, tumors, and cysts.

The main treatment for hydrocephalus is venticuloperitoneal (VP) shunts. The VP shunts are catheters that are surgically lowered through the skull and brain. The VP shunts are then positioned in the lateral ventricle. The distal end of the catheter is tunneled under the skin and positioned in the peritoneal cavity of the abdomen, where the CSF is absorbed.

However, the VP shunts have an extremely high failure rate, e.g., in the range of 30 to 40 percent. Failure includes clogging of the catheter, infection, and faulty pressure valves or one-way valves.

Another relatively newly re-introduced treatment for noncommunicating hydrocephalus is the procedure known as an endoscopic third ventriculostomy (ETV). This procedure involves forming a burr hole in the skull. A probe is passed through the burr hole, through the cerebral cortex, through the underlying white matter and into the lateral and third ventricles. The probe is then used to poke (fenestrate) a hole in the floor of the third ventricle and underlying membrane of Lillequist.

To verify that the procedure is successful, i.e., that a hole is formed in the floor of the third ventricle and the underlying membrane of Lillequist, the patient is observed with a magnetic resonance imaging (MRI) device after the probe poke. The MRI device is used to verify a flow of CSF through the hole in the floor of the third ventricle.

If the MRI device is unable to detect the flow of CSF, a determination is made that a hole in the floor of the third ventricle was not formed, and the ETV procedure is repeated.

Since the MRI device is typically located at a separate location, the ETV procedure typically requires the patient to be moved from location to location. This, in turn, increases the procedure time as well as the expense and complexity of the ETV procedure.

Further, even after successfully forming a hole in the floor of the third ventricle, the hole sometimes closes, typically within two weeks to two months after the ETV procedure. In this event, the patient will have to undergo another ETV procedure or risk serious injury or death.

SUMMARY OF THE INVENTION

An eyelet deployed in a membrane includes: a waist section; a first anchor section coupled to and flared from the waist section; and a second anchor section coupled to and flared from the waist section.

The eyelet is deployed such that the waist section is located within a membrane opening of the membrane. Further, the membrane is sandwiched between the first and second anchor sections. Thus, the eyelet resides generally coplanar with the membrane.

The waist section keeps the membrane opening through which fluid or air can pass open. By sandwiching the membrane, the first and second anchor sections anchor the eyelet to the membrane.

DETAILED DESCRIPTION

In accordance with one embodiment of the present invention, a membrane eyelet 100 (FIGS. 2 and 3A) deployed in a membrane 202 includes: a waist section 102; a first anchor section 104 coupled to and flared from waist section 102; and a second anchor section 106 coupled to and flared from waist section 102.

Figure 2:
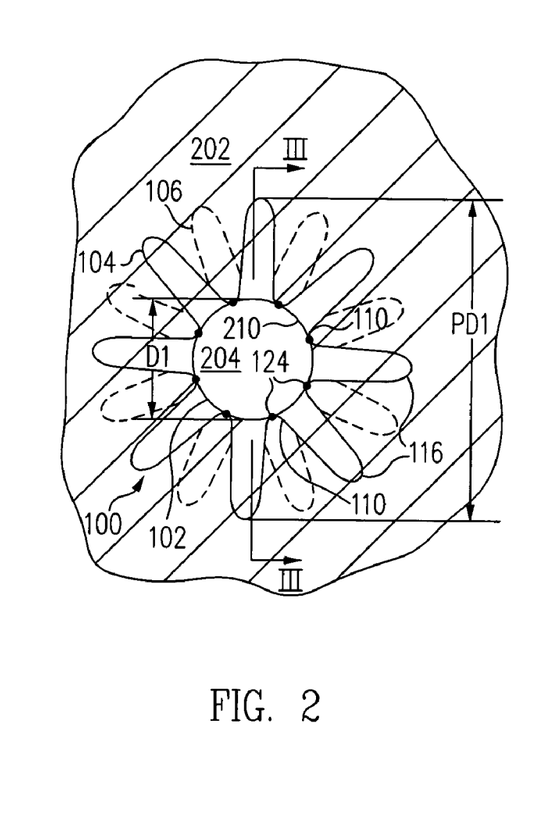
FIG. 2 is a front view of a membrane eyelet deployed in a membrane viewed in the direction II of FIG. 3A, after the membrane eyelet of FIG. 1 has been deployed in a membrane.
Figure 3A:
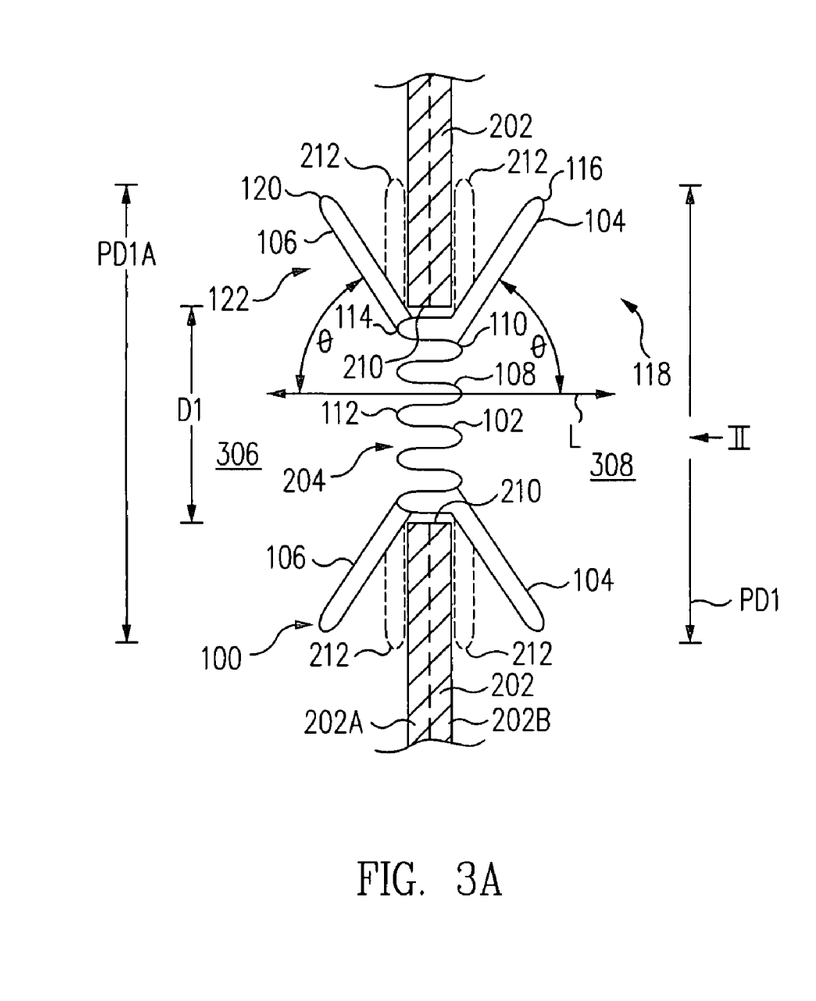
FIG. 3A is a partial cross-sectional view taken at III-III of FIG. 2 of the membrane eyelet deployed within the membrane.

Membrane eyelet 100 is deployed such that waist section 102 is located within a membrane opening 204 of membrane 202. Further, membrane 202 is sandwiched between first and second anchor sections 104, 106.

Waist section 102 keeps membrane opening 204 through which fluid or air can pass open. By sandwiching membrane 202, the first and second anchor sections 104, 106 anchor eyelet 100 to membrane 202.

Figure 1:
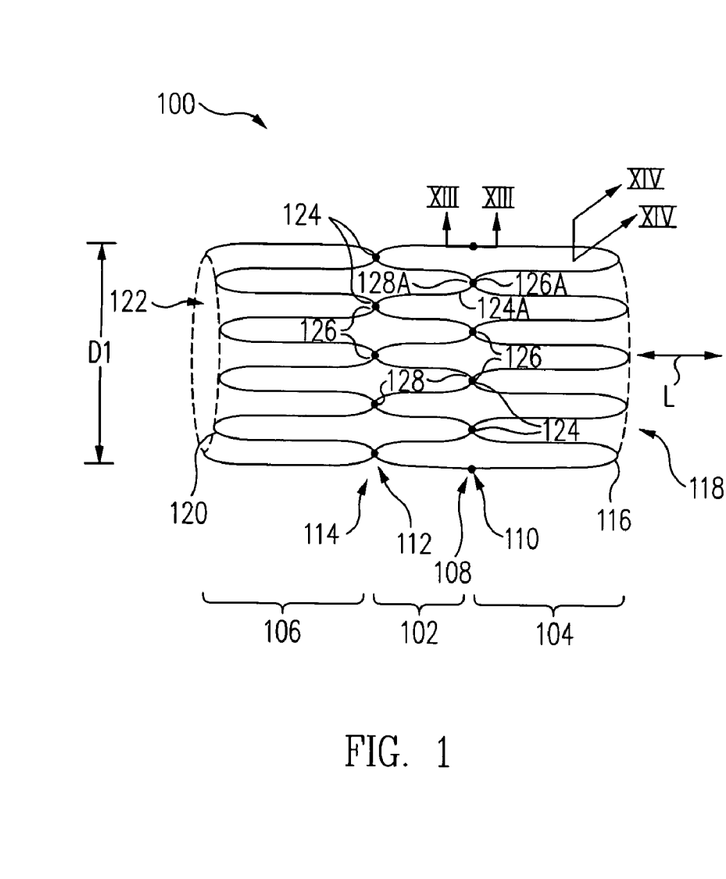
FIG. 1 is a side view showing the front half of a membrane eyelet, prior to deployment, in one embodiment according to the present invention.

More particularly, FIG. 1 is a side view of a membrane eyelet 100, prior to deployment. In FIG. 1, only the near side cylindrical surface of membrane eyelet 100 is illustrated for clarity of illustration, however, it is to be understood that parts of the far side cylindrical surface of membrane eyelet 100 would also be visible.

Referring now to FIG. 1, membrane eyelet 100 includes a waist section 102, a right, e.g., first, anchor section 104, and a left, e.g., second, anchor section 106. Waist section 102 is between and directly coupled to right anchor section 104 and left anchor section 106.

More particularly, waist section 102 includes a right, e.g., first, edge 108 coupled to a left, e.g., first, edge 110 of right anchor section 104. Further, waist section 102 includes a left, e.g., second, edge 112 coupled to a right, e.g., first, edge 114 of left anchor section 106.

Right anchor section 104 further includes a right, e.g., second, edge 116 as represented by the dashed line forming a proximal, e.g., first, end 118 of membrane eyelet 100. Left anchor section 106 further includes a left, e.g., second, edge 120 as represented by the dashed line forming a distal, e.g., second, end 122 of membrane eyelet 100.

Prior to deployment, as shown in FIG. 1, membrane eyelet 100 is cylindrical in shape having a longitudinal axis L. More particularly, waist section 102, right anchor section 104 and left anchor section 106 are rings, sometimes called ring shaped structures. In accordance with one embodiment, membrane eyelet 100 has a first diameter D1 prior to deployment.

FIG. 2 is a front view of membrane eyelet 100 viewed from the direction II of FIG. 3A, after deployment within a membrane 202. FIG. 3A is a partial cross-sectional view taken along III-III of FIG. 2 of membrane eyelet 100 deployed within membrane 202. In FIG. 3A, only top and bottom extending parts of anchor sections 104, 106 are illustrated for clarity of presentation.

As shown in FIGS. 2 and 3A, membrane eyelet 100 is deployed to maintain the patency of an opening 204, sometimes called an aperture, pathway, or orifice, of membrane 202. More particularly, membrane 202 separates a first region 306 from a second region 308. Opening 204 forms a pathway through which fluid or air can pass from first region 306 to second region 308 or vice versa.

Illustratively, membrane 202 is the floor of the third ventricle and membrane eyelet 100 is used to treat hydrocephalus. In accordance with this embodiment, cerebrospinal fluid (CSF) from the 3rd ventricle flows through opening 204 and membrane eyelet 100 into the interpeduncular cistern, thus relieving pressure from the 3rd ventricle. (The underlying membrane of Lillequist is also fenestrated.)

As another example, membrane eyelet 100 is used to support opening 204 through which air flows from a prosthetic airway through to the main brachial airway.

In one embodiment, membrane 202 is a single integral membrane. However, in another embodiment, membrane 202 is formed of two or more membranes (illustratively labeled 202A and 202B and separated by the dashed line in FIG. 3A), which are held together by membrane eyelet 100. For example, membrane 202 is formed of two adjacent blood vessels, arteries, veins or adjacent membranes in the body or any combination thereof. In accordance with this embodiment, membrane eyelet 100 provides fluid transfer such as pressure relief to/from a vessel.

Waist section 102 directly contacts an opening surface 210 of membrane 202. Opening surface 210 defines opening 204. Waist section 102 prevents opening surface 210 from contracting and thus prevents opening 204 from closing. Stated another way, waist section 102 keeps opening 204 open thus preventing constriction of the pathway through which fluid or air can pass from first region 306 to second region 308 or vice versa.

Anchor sections 104 and 106 are flared upon deployment of membrane eyelet 100 to engage membrane 202 thus anchoring membrane eyelet 100 to membrane 202. More particularly, waist section 102 remains cylindrical. However, right anchor section 104 and left anchor section 106 are flared outwards, sometimes called winged, from waist section 102 to sandwich membrane 202 between right anchor section 104 and left anchor section 106. Stated another way, right anchor section 104 and left anchor section 106 wrap around membrane 202 during deployment of membrane eyelet 100. Accordingly, after deployment, membrane eyelet 100 is said to have an eyelet shape.

To illustrate, after deployment of membrane eyelet 100, waist section 102 retains diameter D1. Right anchor section 104 has diameter D1 at left edge 110 and a peripherial diameter PD1 at right edge 116. Peripherial diameter PD1 at right edge 116 of right anchor section 104 is greater than diameter D1 at left edge 110 of right anchor section 104 such that right anchor section 104 flares outwards, sometimes called increases in diameter, from left edge 110 to right edge 116.

To further illustrate, left anchor section 106 has diameter D1 at right edge 114 and a peripherial diameter PD1A at left edge 120. Since peripherial diameter PD1A at left edge 120 of left anchor section 106 is greater than diameter D1 at right edge 114 of left anchor section 106, left anchor section 106 flares outwards, sometimes called increases in diameter, from right edge 114 to left edge 120.

By sandwiching membrane 202 between right anchor section 104 and left anchor section 106, unintentional detachment of membrane eyelet 100 from membrane 202 is avoided.

Generally, an angle θ between longitudinal axis L and planes or conical surfaces defined by anchor sections 104 and 106 is sufficiently large to create overlap or enlargement to prevent unintentional detachment of membrane eyelet 100 from membrane 202.

As shown in FIG. 3A, angle θ is less than 90° in one embodiment such that anchor sections 104 and 106 define conical surfaces. Specifically, right anchor section 104 and/or left anchor section 106 are spaced apart from membrane 202 and do not directly contact membrane 202 or only contact membrane 202 directly adjacent waist section 102. However, right anchor section 104 and/or left anchor section 106 form stops that limit the amount of longitudinal movement (left and/or right movement in the view of FIG. 3A) of membrane eyelet 100.

To illustrate, membrane eyelet 100 is allowed some degree of longitudinal movement in the left direction until right anchor section 104 is pressed into membrane 202 thus preventing further longitudinal movement. Similarly, membrane eyelet 100 is allowed some degree of longitudinal movement in the right direction until left anchor section 106 is pressed into membrane 202 thus preventing further longitudinal movement. However, in yet another embodiment, right anchor section 104 and left anchor section 106 are pressed into membrane 202 upon deployment of membrane eyelet 100 thus preventing any longitudinal motion of membrane eyelet 100.

Further, as indicated by the dashed lines 212, angle θ is equal to or greater than 90° in one embodiment. When angle θ is equal to 90°, right anchor section 104 and left anchor section 106 define planes perpendicular to longitudinal axis L. In accordance with this embodiment, right anchor section 104 and left anchor section 106 are pressed into direct contact with membrane 202.

To deploy membrane eyelet 100, membrane eyelet 100 is inserted into opening 204 such that waist section 102 is located within opening 204. Membrane eyelet 100 is radially expanded to sandwich membrane 202 between right anchor section 104 and left anchor section 106 thus securing waist section 102 within opening 204.

In one embodiment, membrane eyelet 100 is radially expanded using a dilation balloon (not shown) or by a longitudinal compression of a mesh of juxtaposed fibers. Use of dilation balloons and meshes are well known to those of skill in the art and so are not discussed further.

In another embodiment, membrane eyelet 100 is self-expanding where membrane eyelet 100 is constrained within a sheath (not shown). Retraction of the sheath exposes membrane eyelet 100, which self-expands. Use of a sheath to deploy a self-expanding device is well known to those of skill in the art and so is not discussed further.

In one embodiment, right anchor section 104 and left anchor section 106 are selectively expandable relative to waist section 102, i.e., can be radially expanded more than waist section 102. Illustratively, waist section 102 has greater strength than right anchor section 104 and left anchor section 106 such that application of an outwards force, e.g., from a dilation balloon, selectively expands and flares right anchor section 104 and left anchor section 106 relative to waist section 102. To further illustrate, in the example when membrane eyelet 100 is self-expanding, right anchor section 104 and left anchor section 106 are heat set to expand more than waist section 102.

As shown in FIG. 3A, in one embodiment, waist section 102 does not expand, i.e., remains with diameter D1 of FIG. 1, or only expands slightly upon deployment of membrane eyelet 100.

Figure 3B:
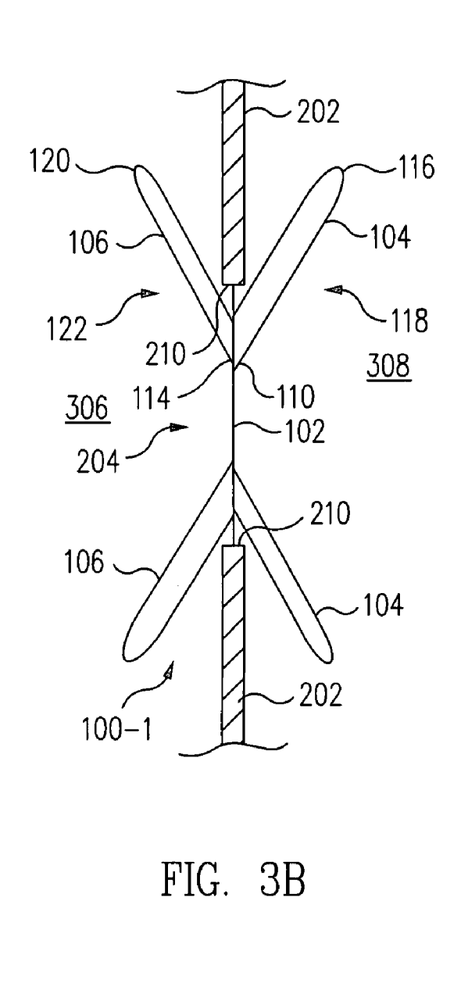
FIG. 3B is a partial cross-sectional view of another membrane eyelet deployed within a membrane as would be seen if that membrane eyelet were viewed as a section cut similar to that taken at III-III in FIG. 2.

FIG. 3B is a partial cross-sectional view as if it were taken at III-III of FIG. 2 of a membrane eyelet 100-1 deployed within membrane 202 in another embodiment according to the present invention. In FIG. 3B, only top and bottom extending parts of anchor sections 104, 106 are illustrated for clarity of presentation.

In accordance with this embodiment, waist section 102 expands to become circularized, i.e., is entirely expanded into the shape of a circle, sometimes called fully expanded. Generally, waist section 102 is fully expanded as illustrated in FIG. 3B, or is partially expanded, i.e., is expanded but less than fully expanded.

Referring again to FIG. 1, right anchor section 104 is a serpentine ring, sometimes called crown. More particularly, right anchor section 104 has a pattern, and this pattern is sometimes called a serpentine pattern, an alternating repeating pattern, or a zigzag pattern.

More particularly, the serpentine pattern extends around a cylindrical surface having longitudinal axis L. Left anchor section 106 is essentially identical to right anchor section 104 though rotationally offset.

Further, waist section 102 has a pattern, and this pattern is sometimes called a serpentine pattern, an alternating repeating pattern, or a zigzag pattern. More particularly, the serpentine pattern extends around a cylindrical surface having longitudinal axis L.

Further, waist section 102 has the same pattern as anchor sections 104, 106, but the height, sometimes called amplitude, of the serpentine pattern of waist section 102 is less than the height of the serpentine patterns of anchor sections 104, 106. However, in another embodiment, the height of the serpentine pattern of waist section 102 is equal to or greater than the height of the serpentine patterns of anchor sections 104, 106.

Anchor sections 104, 106 are connected to waist section 102 by bridges 124. Bridges 124 extend between peaks 126 of the serpentine patterns of anchor sections 104, 106 and peaks 128 of the serpentine pattern of waist section 102. Peaks 126 and 128 are sometimes called minima/maxima of the serpentine patterns of anchor sections 104, 106 and waist section 102, respectively. Bridges 124 can be formed at each adjacent peak 126 and 128, or only at some (fewer than all) of peaks 126 and 128.

To illustrate, a first bridge 124A of the plurality of bridges 124 extends between a first peak 126A of the plurality of peaks 126 of the serpentine pattern of right anchor section 104 and a first peak 128A of the plurality of peaks 128 of the serpentine pattern of waist section 102.

Although waist section 102 is illustrated as a single serpentine ring in FIG. 1, in another embodiment, a waist section is simply defined as the region of connection between right anchor section 104 and left anchor section 106 as discussed further below in reference to FIGS. 4, 5 and 6. It yet another embodiment, a waist section includes a plurality of interconnected serpentine rings as discussed further below in reference to FIGS. 7 and 8.

Further, although various expandable elements are described as serpentine rings, the expandable elements can be formed in other expandable patterns in other embodiments such as in a zigzag or diamond shaped pattern.

Figure 4:
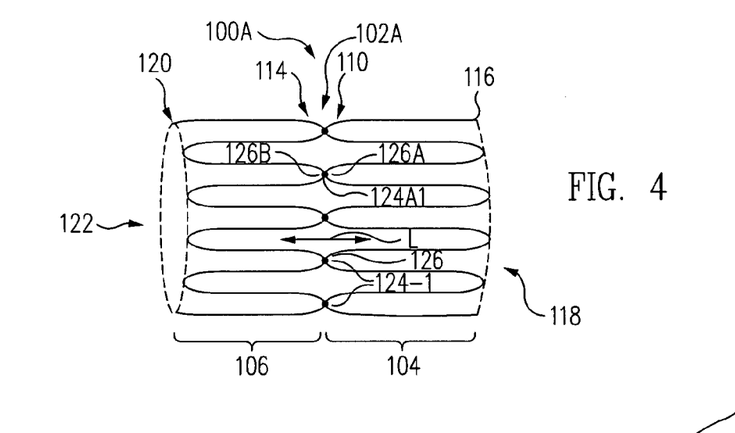
FIG. 4 is a side view of a membrane eyelet, prior to deployment, in one embodiment according to the present invention.

FIG. 4 is a side view of a membrane eyelet 100A, prior to deployment, in one embodiment according to the present invention. In FIG. 4, only the near side cylindrical surface of membrane eyelet 100A is illustrated for clarity of illustration, however, it is to be understood that parts of the far side cylindrical surface of membrane eyelet 100A would also be visible.

As shown in FIG. 4, membrane eyelet 100A includes right anchor section 104 and left anchor section 106 as discussed above in reference to FIG. 1. However, in accordance with this embodiment, anchor sections 104, 106 are directly connected to one another by bridges 124-1, which define a waist section 102A. Bridges 124-1 extend between peaks 126 of the serpentine patterns of anchor sections 104, 106.

To illustrate, a first bridge 124A-1 of the plurality of bridges 124-1 extends between first peak 126A of the serpentine pattern of right anchor section 104 and a first peak 126B of the plurality of peaks 126 of the serpentine pattern of left anchor section 106.

Figure 5:
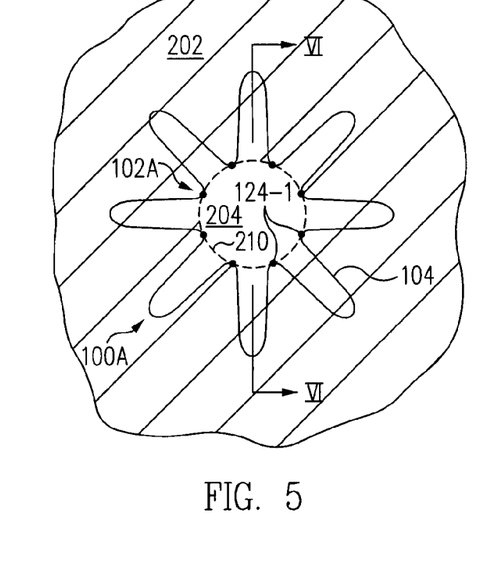
FIG. 5 is a front view of the membrane eyelet viewed in the direction V of FIG. 6, after the membrane eyelet of FIG. 4 has been deployed within a membrane.
Figure 6:
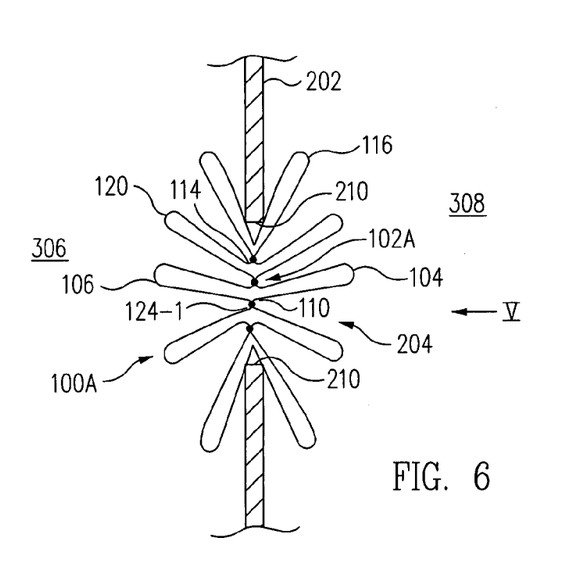
FIG. 6 is a cross-sectional view taken at VI-VI of FIG. 5 of the membrane eyelet deployed within the membrane.

FIG. 5 is a front view of membrane eyelet 100A taken from the direction V of FIG. 6, after deployment within membrane 202. FIG. 6 is a cross-sectional view taken at VI-VI of FIG. 5 of membrane eyelet 100A deployed within membrane 202.

Referring now to FIGS. 5 and 6 together, bridges 124-1 directly contact opening surface 210 of membrane 202. More generally, waist section 102A directly contacts opening surface 210 of membrane 202.

Bridges 124-1 prevent opening surface 210 from contracting and thus prevents opening 204 from closing. Stated another way, bridges 124-1 keeps opening 204 open thus preventing constriction of the pathway through which fluid or air can pass from first region 306 to second region 308 or vice versa.

Figure 7:
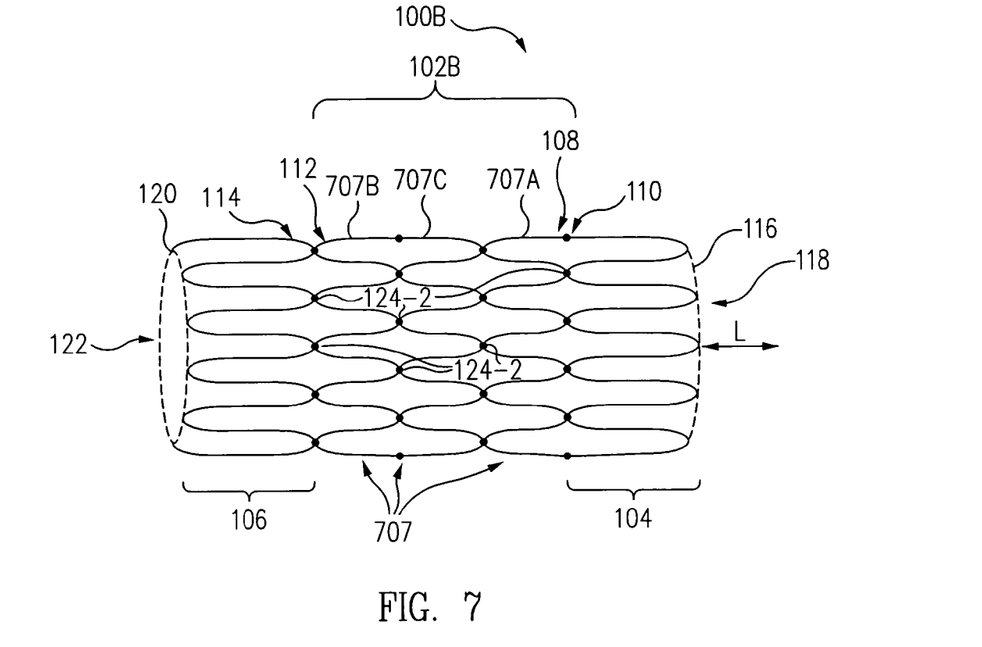
FIG. 7 is a side view of a membrane eyelet, prior to deployment, in one embodiment according to the present invention.

FIG. 7 is a side view of a membrane eyelet 100B, prior to deployment, in one embodiment according to the present invention. In FIG. 7, only the near side cylindrical surface of membrane eyelet 100B is illustrated for clarity of illustration, however, it is to be understood that parts of the far side cylindrical surface of membrane eyelet 100B would also be visible.

As shown in FIG. 7, membrane eyelet 100B includes right anchor section 104 and left anchor section 106 as discussed above. However, in accordance with this embodiment, anchor sections 104, 106 are directly connected by bridges 124-2 to a waist section 102B, which includes a plurality, e.g., three, of serpentine rings 707.

More particularly, right anchor section 104 is directly connected by bridges 124-2 to a first serpentine ring 707A of the plurality of serpentine rings 707. Left anchor section 106 is directly connected by bridges 124-2 to a second serpentine ring 707B of the plurality of serpentine rings 707. Serpentine rings 707A, 707B are directly connected by bridges 124-2 to a third serpentine ring 707C of the plurality of serpentine rings 707.

Although waist section 102B is illustrated and discussed above as including three serpentine rings 707A, 707B, and 707C, those of skill in the art will understand in light of this disclosure that a waist section can be formed having more or less than three interconnected serpentine rings.

Figure 8:
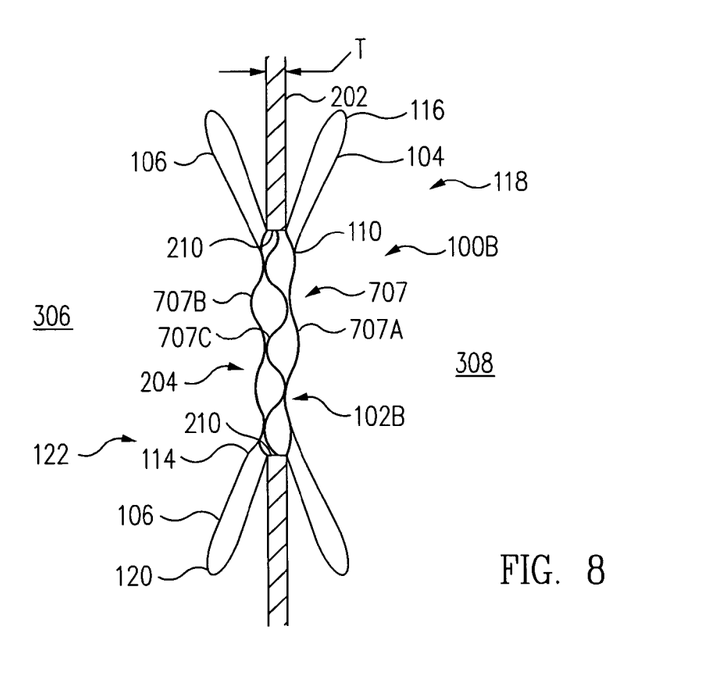
FIG. 8 is a partial cross-sectional view of the membrane eyelet of FIG. 7, after deployment within a membrane.

FIG. 8 is a partial cross-sectional view of membrane eyelet 100B of FIG. 7, after deployment within membrane 202. Referring now to FIG. 8, serpentine rings 707 directly contact opening surface 210 of membrane 202. More generally, waist section 102B directly contacts opening surface 210 of membrane 202.

Serpentine rings 707 prevent opening surface 210 from contracting and thus prevent opening 204 from closing. Stated another way, serpentine rings 707 keep opening 204 open thus preventing constriction of the pathway through which fluid or air can pass from first region 306 to second region 308 or vice versa.

Illustratively, by forming waist section 102B with a plurality of serpentine rings 707, waist section 102B is well suited to support opening surface 210 in the case when the thickness T of membrane 202 is relatively large.

Although right anchor section 104 is illustrated as a single serpentine ring in FIG. 1, in another embodiment, right anchor section 104 includes a plurality of serpentine rings as discussed further below in reference to FIGS. 9 and 10.

Figure 9:
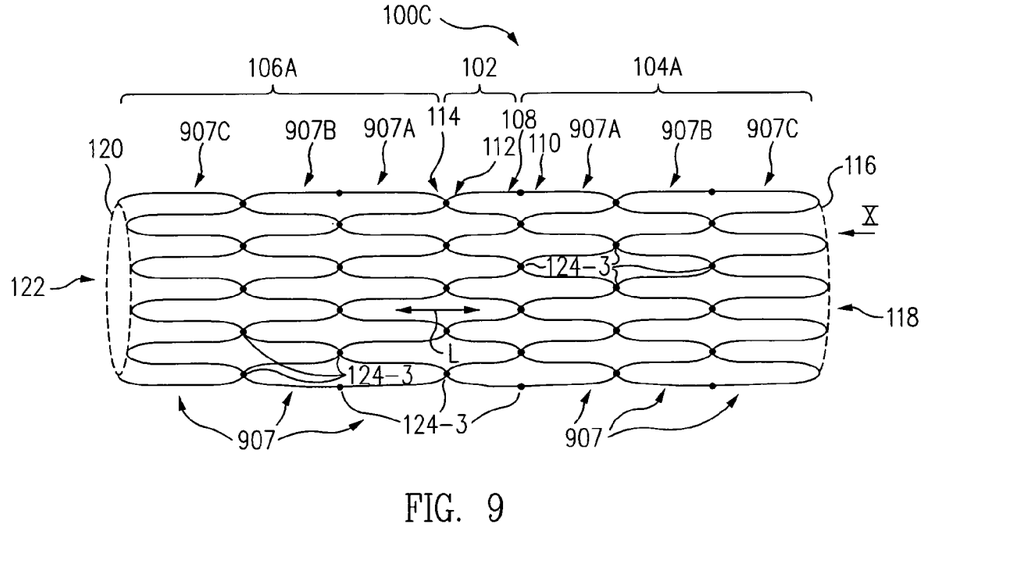
FIG. 9 is a side view of a membrane eyelet, prior to deployment, in one embodiment according to the present invention.

FIG. 9 is a side view of a membrane eyelet 100C, prior to deployment, in one embodiment according to the present invention. In FIG. 9, only the near side cylindrical surface of membrane eyelet 100C is illustrated for clarity of illustration, however, it is to be understood that parts of the far side cylindrical surface of membrane eyelet 100C would also be visible.

As shown in FIG. 9, membrane eyelet 100C includes waist section 102 as discussed above in reference to FIG. 1. Waist section 102 is directly connected by bridges 124-3 to a right anchor section 104A and a left anchor section 106A. However, in accordance with this embodiment, anchor sections 104A, 106B each include a plurality, e.g., three, of serpentine rings 907.

More particularly, waist section 102 is directly connected by bridges 124-3 to a first serpentine ring 907A of the plurality of serpentine rings 907 of right anchor section 104A. First serpentine ring 907A is directly connected by bridges 124-3 to a second serpentine ring 907B of the plurality of serpentine rings 907 of right anchor section 104A.

Similarly, second serpentine ring 907B is directly connected by bridges 124-3 to a third serpentine ring 907C of the plurality of serpentine rings 907 of right anchor section 104A. Third serpentine ring 907C defines right edge 116 of right anchor section 104A and forms proximal end 118 of membrane eyelet 100C.

Further, waist section 102 is directly connected by bridges 124-3 to a first serpentine ring 907A of the plurality of serpentine rings 907 of left anchor section 106A. First serpentine ring 907A is directly connected by bridges 124-3 to a second serpentine ring 907B of the plurality of serpentine rings 907 of left anchor section 106A.

Similarly, second serpentine ring 907B is directly connected by bridges 124-3 to a third serpentine ring 907C of the plurality of serpentine rings 907 of left anchor section 106A. Third serpentine ring 907C defines left edge 120 of left anchor section 106A and forms distal end 122 of membrane eyelet 100C.

Although anchor sections 104A, 106A are illustrated and discussed above as each including three serpentine rings 907A, 907B, and 907C, those of skill in the art will understand in light of this disclosure that an anchor section can be formed having more, e.g., up to 50, or less than three interconnected serpentine rings.

Figure 10:
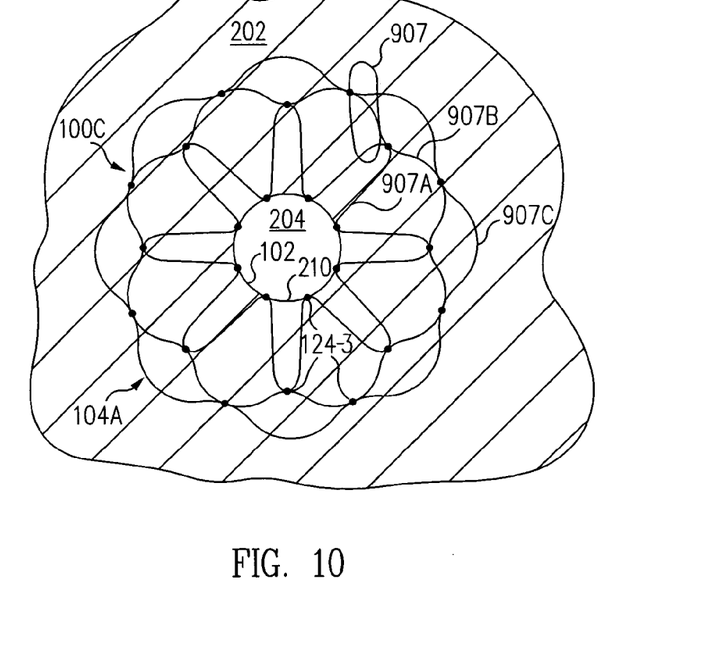
FIG. 10 is a front view of the membrane eyelet of FIG. 9 deployed in a membrane.

FIG. 10 is a front view of membrane eyelet 100C viewed from the line X of FIG. 9, after deployment within membrane 202. Referring now to FIG. 10, serpentine rings 907 of right anchor section 104A become progressively larger, i.e., have a larger average diameter, from first serpentine ring 907A to third serpentine ring 907C. Due to this progressive increase in size, once deployed, right anchor section 104A is sometimes said to be flower shaped. Illustratively, by using serpentine rings 907 having different properties, e.g., by forming serpentine ring 907C to be relatively thin and easily deformable compared to serpentine ring 907A, selective (more or less) flaring of right anchor section 104A is obtained. Left anchor section 106A is essentially identical in shape and function to right anchor section 104A and so is not illustrated or discussed for simplicity.

Figure 11:
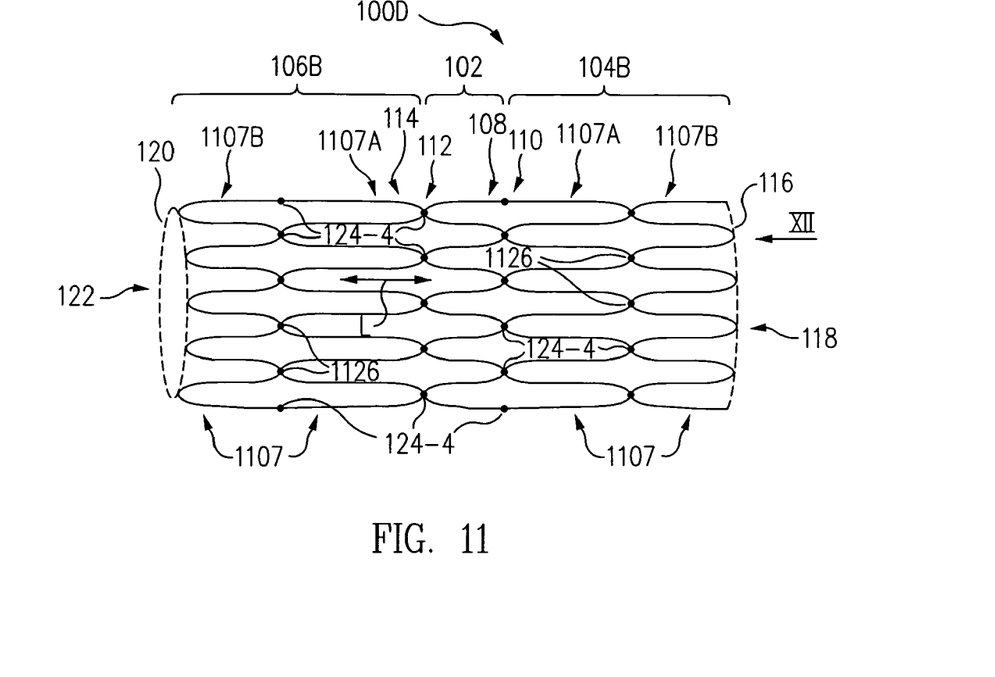
FIG. 11 is a side view of a membrane eyelet, prior to deployment, in one embodiment according to the present invention.

FIG. 11 is a side view of a membrane eyelet 100D, prior to deployment, in one embodiment according to the present invention. In FIG. 11, only the near side cylindrical surface of membrane eyelet 100D is illustrated for clarity of illustration, however, it is to be understood that parts of the far side cylindrical surface of membrane eyelet 100D would also be visible.

As shown in FIG. 11, membrane eyelet 100D includes waist section 102 as discussed above in reference to FIG. 1. Waist section 102 is directly connected by bridges 124-4 to a right anchor section 104B and a left anchor section 106B. However, in accordance with this embodiment, anchor sections 104B, 106B include a plurality, e.g., two, serpentine rings 1107.

More particularly, waist section 102 is directly connected by bridges 124-4 to a first serpentine ring 1107A of the plurality of serpentine rings 1107 of right anchor section 104B. First serpentine ring 1107A is directly connected by bridges 124-4 to a second serpentine ring 1107B of the plurality of serpentine rings 1107 of right anchor section 104B. Second serpentine ring 1107B defines right edge 116 of right anchor section 104B and forms proximal end 118 of membrane eyelet 100D.

Further, waist section 102 is directly connected by bridges 124-4 to a first serpentine ring 1107A of the plurality of serpentine rings 1107 of left anchor section 106B. First serpentine ring 1107A is directly connected by bridges 124-4 to a second serpentine ring 1107B of the plurality of serpentine rings 1107 of left anchor section 104B. Second serpentine ring 1107B defines left edge 120 of left anchor section 106B and forms distal end 122 of membrane eyelet 100D.

Figure 12:
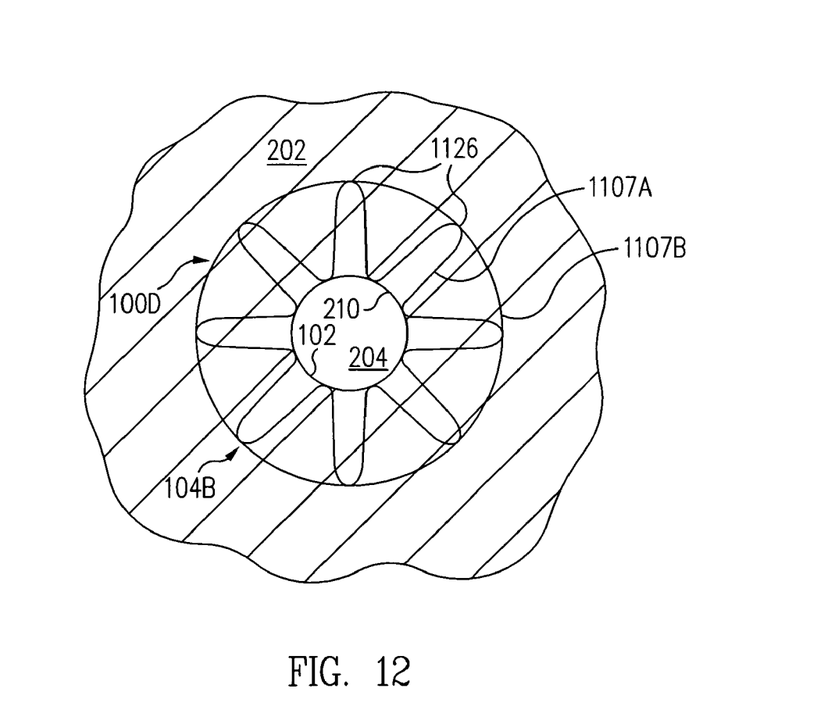
FIG. 12 is a front view of the membrane eyelet of FIG. 11, after deployment within a membrane.

FIG. 12 is a front view of membrane eyelet 100D viewed from the line XII of FIG. 11, after deployment within membrane 202. Referring to FIGS. 11 and 12 together, second serpentine ring 1107B of right anchor section 104B is sometimes called a stabilizing ring 1107B. More particularly, stabilizing ring 1107B becomes circularized, i.e., fully expanded to become a circle, upon deployment of membrane eyelet 100D.

Stabilizing ring 1107B connects peaks 1126 of first serpentine ring 1107A thus providing stability and strength to first serpentine ring 1107A. Further, by enclosing peaks 1126 of first serpentine ring 1107A, stabilizing ring 1107B minimizes the possibility of the device used to deploy membrane eyelet 100D from catching on peaks 1126 of first serpentine ring 1107A and the associated unintentional detachment of membrane eyelet 100D from membrane 202.

Left anchor section 106B is essentially identical in shape and function to right anchor section 104B and so is not illustrated or discussed further for simplicity.

Referring again to FIG. 1, in one embodiment, membrane eyelet 100 is integral, i.e., is a single piece and not a plurality of separate pieces connected together. For example, membrane eyelet 100 is formed by laser cutting a tubular piece of material.

However, in an alternative embodiment, waist section 102, right anchor section 104, and left anchor section 106 are separate pieces, which are connected together, e.g., by welding.

In one embodiment, membrane eyelet 100 is formed from: 1) stainless-steel; 2) chromium alloy; 3) a shape memory alloy such as nickel titanium that has been heat-set, or tempered, in such a manner to provide membrane eyelet 100 with an inherent self-expanding characteristic; and/or 4) polymer; and/or 5) a combination thereof, although other materials are used in other embodiments.

To illustrate, waist section 102, right anchor section 104, and left anchor section 106 are formed from the same material.

Alternatively, right anchor section 104, and left anchor section 106 are formed from the same material. However, waist section 102 is formed of a material different than the material of right anchor section 104 and left anchor section 106.

Figure 13A:
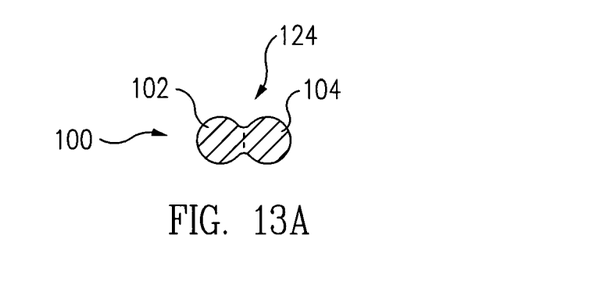
FIG. 13A is a cross-sectional view of a bridge of the membrane eyelet of FIG. 1 taken at XIII-XIII.

FIG. 13A is a cross-sectional view of bridge 124 of membrane eyelet 100 of FIG. 1 taken at XIII-XIII. In accordance with this embodiment, waist section 102 and right anchor section 104 are formed of the same material, e.g., a metallic, and this material is coupled, e.g., welded, fused, or otherwise joined, to form bridge 124.

Figure 13B:
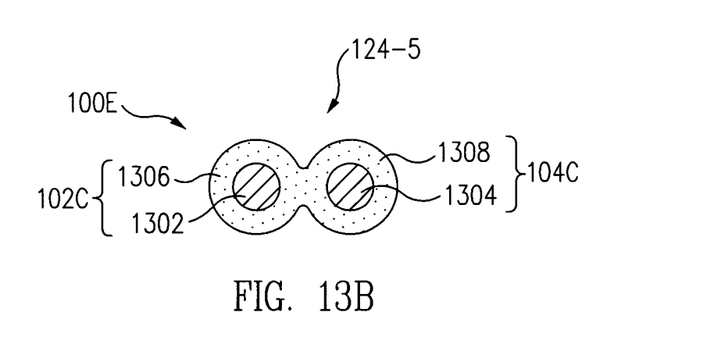
FIGS. 13B and 13C are cross-sectional views of bridges of membrane eyelets similar to the membrane eyelet of FIG. 1.

FIG. 13B is a cross-sectional view of a bridge 124-5 of a membrane eyelet 100E similar to membrane eyelet 100 of FIG. 1. Waist section 102C and a right anchor section 104C are formed of a polymer coated metallic, e.g., a nylon coated steel.

More particularly, waist section 102C and right anchor section 104C include first and second metallic cores 1302, 1304 and first and second polymers 1306, 1308 enclosing and covering metallic cores 1302, 1304, respectively. Polymer 1306 of waist section 102C and polymer 1308 of right anchor section 104C are coupled, e.g., welded, fused, or otherwise joined, to form bridge 124-5. However, metallic cores 1302 and 1304 are not directly connected, but spaced apart.

Figure 13C:
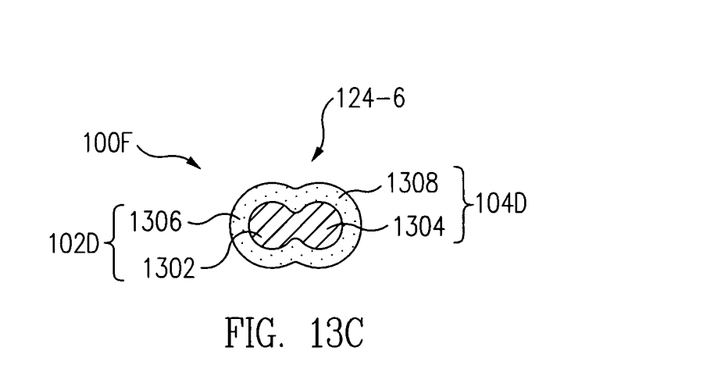

FIG. 13C is a cross-sectional view of bridge 124-6 of a membrane eyelet 100F similar to membrane eyelet 100 of FIG. 1. A waist section 102D and a right anchor section 104D are formed of a polymer coated metallic, e.g., a nylon coated steel.

More particularly, waist section 102D and right anchor section 104D include metallic cores 1302, 1304 and polymers 1306, 1308 enclosing and covering metallic cores 1302, 1304, respectively. Polymer 1306 of waist section 102D and polymer 1308 of right anchor section 104D are coupled, e.g., welded, fused, or otherwise joined. Further, metallic core 1302 of waist section 102D and metallic core 1304 of right anchor section 104D are also coupled, e.g., welded, fused, or otherwise joined. Thus, bridge 124-6 is formed by the collective joining of polymer 1306, metallic core 1302 of waist section 102D to polymer 1308, metallic core 1304 of right anchor 104D, respectively.

Although a single bridge 124 is illustrated and discussed in FIG. 13A, in light of this disclosure, those of skill in the art will understand that the other bridges 124 of membrane eyelet 100 of FIG. 1 are formed similarly.

Figure 14:
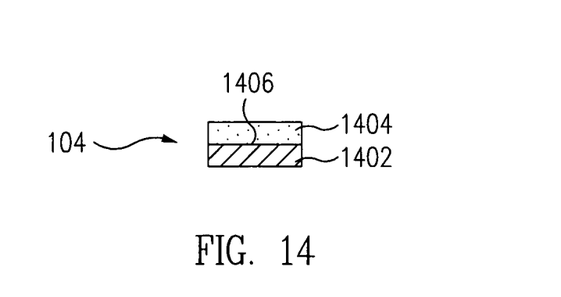
FIG. 14 is a cross-sectional view of the membrane eyelet of FIG. 1 taken at XIV-XIV.
Figure 15:
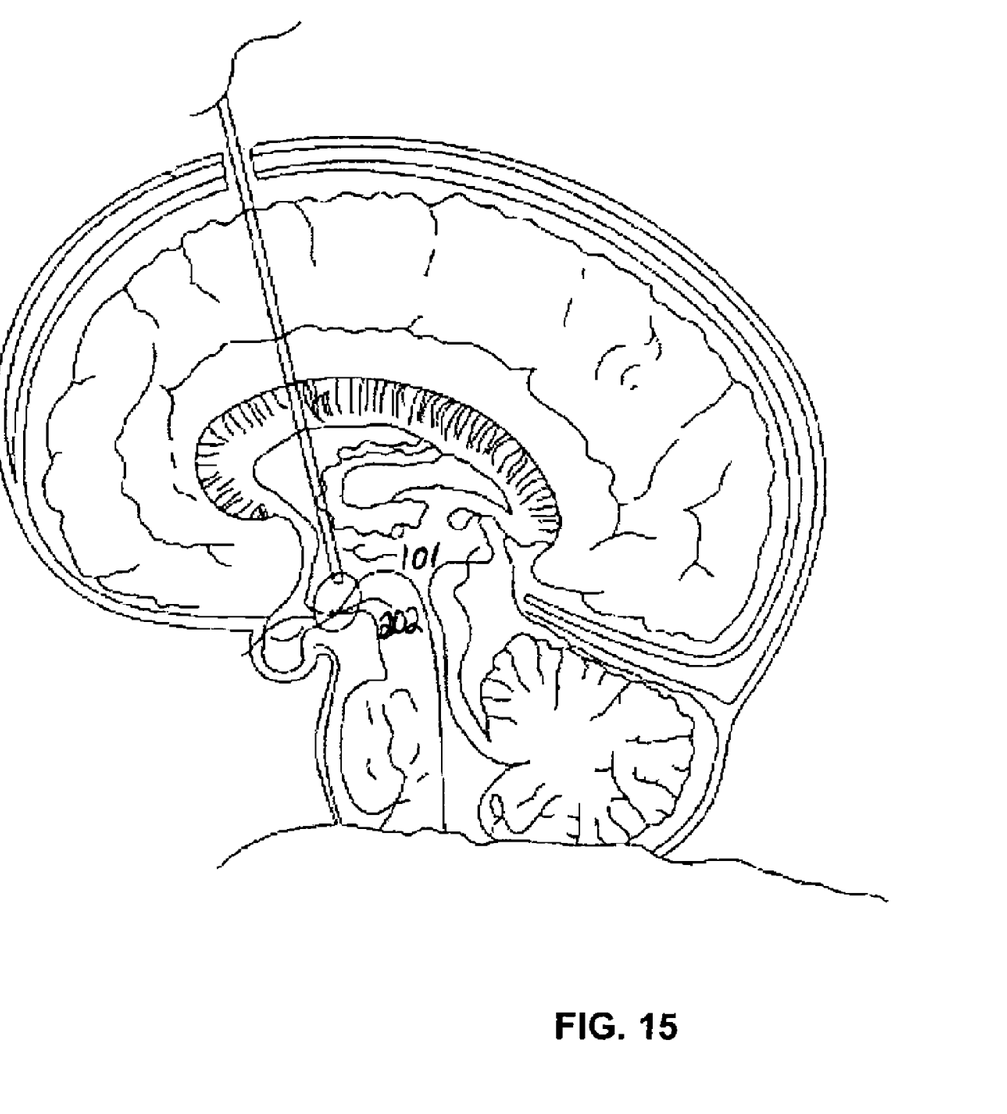
FIG. 15 is a cross-sectional view of a human cranium during an endoscopic third ventriculostomy procedure using an endoscopic third ventriculostomy probe in one embodiment according to the present invention.

FIG. 14 is a cross-sectional view of membrane eyelet 100 of FIG. 1 taken at XIV-XIV. Membrane eyelet 100 is formed from a polymer-metallic laminate. Accordingly, membrane eyelet 100 is sometimes called a laminate structure.

More particular, membrane eyelet 100 includes a metallic core 1402 and a polymer 1404 on and coating a surface 1406 of metallic core 1402. Surface 1406 is either the outer cylindrical surface or the inner cylindrical surface of membrane eyelet 100.

A method according to the invention includes inserting a membrane eyelet into an opening of a membrane such that a waist section of the membrane eyelet is located in the opening and radially expanding the membrane eyelet such that the membrane is sandwiched between a first anchor section and a second anchor section of the membrane eyelet, where the step of radially expanding includes flaring the first anchor section and the second anchor section from the waist section, where the membrane can be the floor of the third ventricle.

Another method includes placing a stent into an opening in the floor of the third ventricle. The stent is deployed into the opening. The stent prevents the opening from closing. The stent includes expanded ends that prevent the stent from becoming disengaged from the floor.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A method comprising:
   forming a burr hole in a skull;
   inserting a probe through the burr hole to the third ventricle of the brain;
   generating an opening through the floor of the third ventricle with the probe;
   inserting a stent supported by the probe into the opening in the floor of the third ventricle, and deploying said stent within the opening, wherein said stent prevents said opening from closing.

2. The method of claim 1 further comprising forming said opening is said floor of said third ventricle.

3. The method of claim 1 wherein said floor separates a first region from a second region.

4. The method of claim 1 wherein said stent has expanded ends which engage said stent with said floor.

5. The method of claim 4 wherein said expanded ends of said stent prevent said stent from being disengaged from said floor.

* * * * *